(12) United States Patent  
Ou Yang et al.

(10) Patent No.: US 8,199,008 B2  
(45) Date of Patent: Jun. 12, 2012

(54) PERSONAL ALARM SYSTEM

(75) Inventors: Ming-Shiu Ou Yang, Taipei Hsien (TW); Chung-Jen Hsieh, Taipei Hsien (TW)

(73) Assignee: Hon Hai Precision Industry Co., Ltd., Tu-Cheng, New Taipei (TW)

( * ) Notice: Subject to any disclaimer, the term of this patent is extended or adjusted under 35 U.S.C. 154(b) by 371 days.

(21) Appl. No.: 12/562,077

(22) Filed: Sep. 17, 2009

(65) Prior Publication Data

US 2011/0037594 A1    Feb. 17, 2011

(30) Foreign Application Priority Data

Aug. 14, 2009 (CN) .......................... 2009 1 0305662

(51) Int. Cl.  
*G08B 21/00* (2006.01)

(52) U.S. Cl. ..................... 340/540; 340/541; 340/309.4; 340/309.7; 340/309.16; 340/573.1; 340/691.1; 177/12; 177/45; 177/48; 177/117

(58) Field of Classification Search .................. 340/540, 340/541, 309.4, 309.7, 309.16, 345.1, 573.1, 340/691.1; 177/12, 45, 48, 117  
See application file for complete search history.

(56) References Cited

U.S. PATENT DOCUMENTS

| | | | | |
|---|---|---|---|---|
| 4,303,801 A | * | 12/1981 | Anderson et al. | 379/47 |
| 7,868,743 B1 | * | 1/2011 | Brown | 340/309.4 |
| 2008/0259742 A1 | * | 10/2008 | Tadanori | 368/263 |

* cited by examiner

*Primary Examiner* — Tai T Nguyen  
(74) *Attorney, Agent, or Firm* — Altis Law Group, Inc.

(57) ABSTRACT

A personal alarm system can help a user to wake up in a preset time. A sensor can sense operations of the personal alarm system and output sense signals. A control unit can calculate a sum of the sense signals to obtain a number of operations of the personal alarm system, and stop an alarm from sounding in response to the sum of the sense signals meeting the condition to stop the alarm from sounding.

7 Claims, 2 Drawing Sheets

PERSONAL ALARM SYSTEM

BACKGROUND

1. Technical Field

The present disclosure relates to alarm systems, and particularly to a personal alarm system with an alarm clock which sounds an alarm at a predetermined time.

2. Description of Related Art

Many people use devices with alarm clocks to help them waking up in the morning. A normal method of operation is that a user set a time to a device with an alarm clock. When a timer in the device matches the time set by the user, the device sounds an alarm. The user can stop the alarm from sounding, normally by pressing a button on the device. However, if the user is in deep sleep or too tired, he or she might press the button to stop the alarm from sounding without actually getting up, therefore, this method can not efficiently awake the user from sleep.

DETAILED DESCRIPTION

Figure 1:
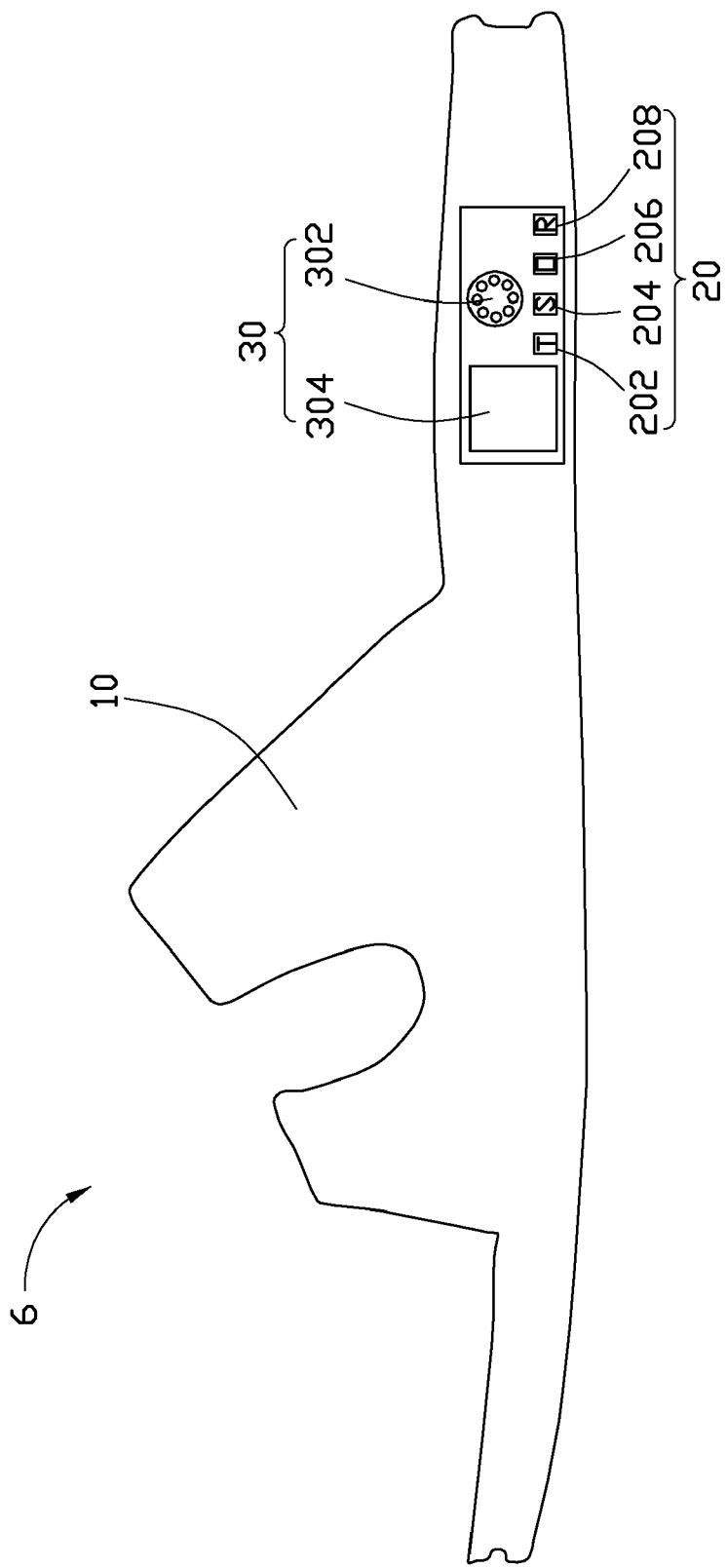
FIG. 1 is a schematic diagram of an exemplary embodiment of a personal alarm system.
Figure 2:
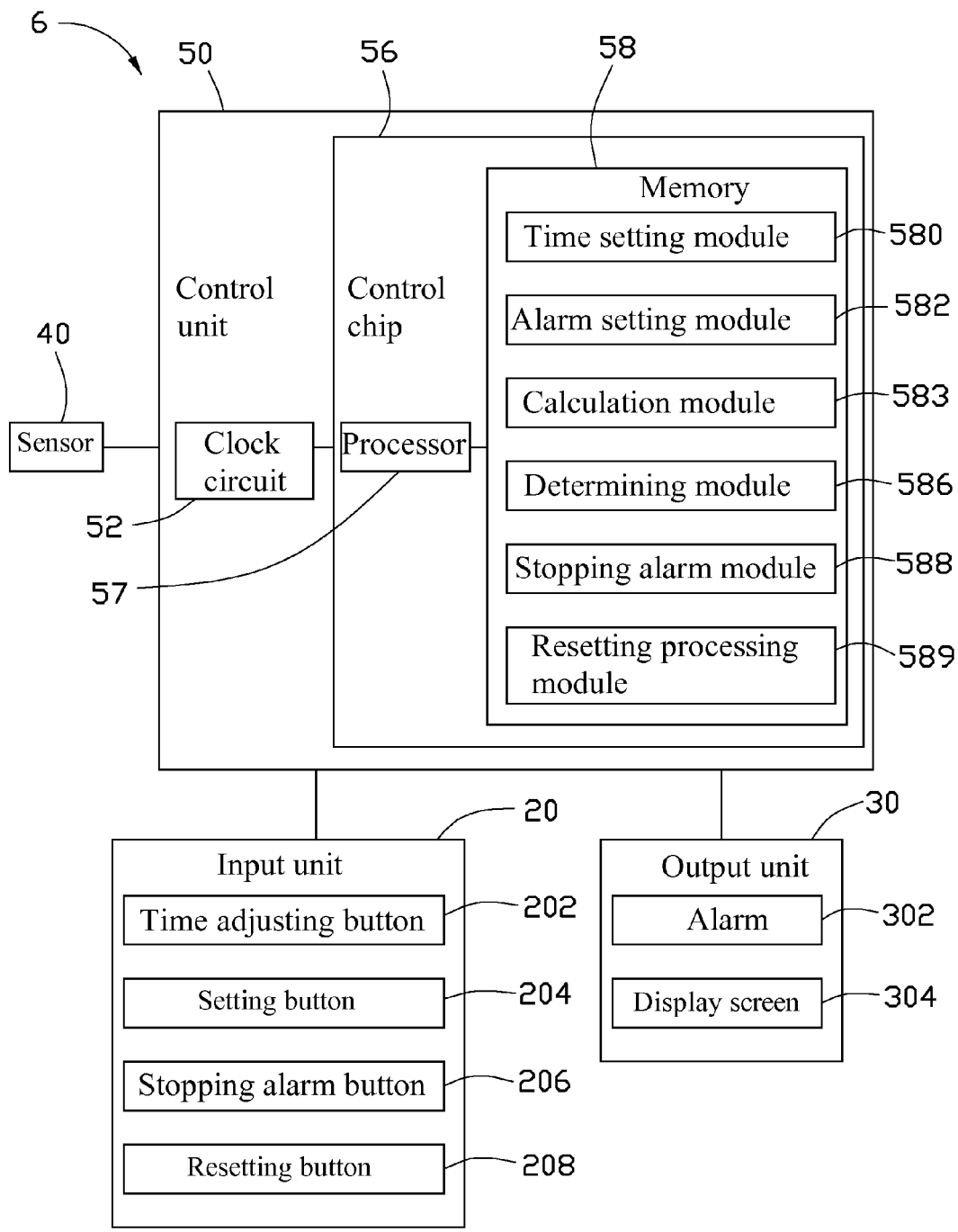
FIG. 2 is a block diagram of the personal alarm system of FIG. 1.

Referring to FIGS. 1 and 2, an exemplary embodiment of a personal alarm system 6 includes a main body 10 (a sandal, for example), an input unit 20 and an output unit 30 both set on the outside of the main body 10, and a sensor 40 and a control unit 50 both set inside the main body 10. The control unit 50 is connected to the input unit 20, the output unit 30, and the sensor 40. In one embodiment, the personal alarm system 6 may be formed on a shoe or another kind of personal device.

The input unit 20 includes a time adjusting button 202, a setting button 204, a stopping alarm button 206, and a resetting button 208. The time adjusting button 202, the setting button 204, the stopping alarm button 206, and the resetting button 208 can receive information input by users and send input signals corresponding to the information to the control unit 50. In detail, the time adjusting button 202 can receive a current time, such as 21:20 input by users. The setting button 204 can receive a time (e.g., 7:30) to sound an alarm, and a condition to stop the alarm from sounding, input by users. In one embodiment, the condition to stop the alarm from sounding can be a number of vibrations of the main body 10 exceeding seven times. The stopping alarm button 206 can control to stop the alarm from sounding. The resetting button 208 can receive resetting operations input by users, for example, a resetting operation may be that the time to sound the alarm is set to zero. In other embodiments, the stopping alarm button 206 and the resetting button 208 can also be omitted according to requirements.

The output unit 30 includes an alarm 302 and a display screen 304. The alarm 302 can sound controlled by the control unit 50. The display screen 304 can display corresponding information, such as the current time or the time to sound the alarm 302, controlled by the control unit 50.

The sensor 40 can sense operations of the main body 10, and send corresponding sense signals to the control unit 50. In one embodiment, the sensor 40 can be a pressure sensor, a mechanical shock sensor, or another kind of sensor. For example, if the sensor 40 is a pressure sensor and the personal alarm system 6 is formed on a shoe, a user wears the shoe and walks to exert pressure on a bottom of the main body 10, the sensor 40 can sense the pressure and send corresponding pressure signals to the control unit 50. If the sensor 40 is a mechanical shock sensor, the user wears the shoe and walks, the sensor 40 can sense every vibration of the shoe and send corresponding vibration signals to the control unit 50.

The control unit 50 includes a clock circuit 52 for timing and a control chip 56. The control chip 56 includes a processor 57 and a memory 58 connected to the processor 57. The memory 58 includes a time setting module 580, an alarm setting module 582, a calculation module 583, a determining module 586, a stopping alarm module 588, and a resetting processing module 589, each of which stores one or more computerized instructions to be executed by the processor 57.

The time setting module 580 receives the current time by pressing the time adjusting button 202, and displays the current time on the display screen 304.

The alarm setting module 582 receives the time (e.g., 7:30) to sound the alarm 302 by pressing the setting button 204 and the condition to stop the alarm 302 from sounding, for example, the condition to stop the alarm 302 from sounding may be the number of vibrations of the personal alarm system 6 exceeding 7 times or the number of vibrations of the personal alarm system 6 exceeding 30 times within a period of time (e.g., 20 seconds), and displays the time (e.g., 7:30) to sound the alarm 302 and the condition (e.g., 7 times or 20 seconds and 30 times) to stop the alarm 302 from sounding on the display screen 304. The alarm setting module 582 also controls to sound the alarm 302 in response to the time (e.g., 7:30) to sound the alarm 302 timed by the time circuit 52 being reached. The alarm setting module 582 also sends a timing stopping signal to the determining module 586 when the condition to stop the alarm 302 from sounding is the number of vibrations of the personal alarm system 6 exceeding 30 times within a period of time and the period of time being reached.

The calculation module 583 receives the sense signals from the sensor 40 and calculates a sum of the sense signals to obtain the number of vibrations (e.g., 7 times) of the personal alarm system 6. For example, if the personal alarm system 6 is formed on a shoe, a user wears the shoe and walks, the main body 10 of the shoe vibrates up and down, the sensor 40 senses every vibration of the shoe and sends the corresponding sense signals to the calculation module 583 of the control unit 50.

The determining module 586 determines whether the sum of the sense signals meets the condition to stop the alarm 302 from sounding, for example, the condition to stop the alarm 302 from sounding is that the number of vibrations is 7 times. The determining module 586 also receives the timing stopping signal and determines whether the sum of the sense signals meets the condition to stop the alarm 302 from sounding, and stops the alarm 302 from sounding in response to the sum of the sense signals meeting the condition.

The stopping alarm module 588 stops the alarm 302 from sounding by pressing the stopping alarm button 206.

The resetting processing module 589 receives resetting operations by pressing the resetting button 208, displays corresponding resetting operation information on the display screen 304. For example, a resetting operation may be that the time to sound the alarm 302 is set to zero.

It is to be understood, however, that even though numerous characteristics and advantages of the embodiments have been set forth in the foregoing description, together with details of the structure and function of the embodiments, the disclosure is illustrative only, and changes may be made in details, especially in matters of shape, size, and arrangement of parts within the principles of the embodiments to the full extent indicated by the broad general meaning of the terms in which the appended claims are expressed.

What is claimed is:

1. A personal alarm system, comprising:
an input unit comprising a setting button;
an output unit comprising an alarm and a display screen;
a sensor to sense operations of the personal alarm system and output sense signals; and
a control unit connected to the input unit, the output unit, and the sensor, and comprising a clock circuit and a control chip, wherein the control chip comprises a processor and a memory connected to the processor, the memory comprising a plurality of modules each of which stores one or more computerized instructions which the processor executes, the plurality of modules comprises:
an alarm setting module to receive a time to sound the alarm by pressing the setting button and a condition to stop the alarm from sounding, and control to sound the alarm in response to the time to sound the alarm timed by the time circuit being reached;
a calculation module to receive the sense signals from the sensor, and calculate a sum of the sense signals to obtain number of operations of the personal alarm system; and
a determining module to determine whether the sum of the sense signals meets the condition to stop the alarm from sounding, and stop the alarm from sounding in response to the sum of the sense signals meeting the condition.

2. The system of claim 1, further comprising a main body, wherein the input unit and the output unit are set on the outside of the main body, the sensor and the control unit are set inside of the main body.

3. The system of claim 1, wherein the sensor is a pressure sensor, the sensor senses pressure on the personal alarm system and sends pressure signals to the control unit.

4. The system of claim 1, wherein the sensor is a mechanical shock sensor, the sensor senses every vibration of the personal alarm system and sends vibration signals to the control unit.

5. The system of claim 1, wherein the condition to stop the alarm from sounding is the number of vibrations of the personal alarm system exceeding preset times.

6. The system of claim 1, wherein the condition to stop the alarm from sounding is the number of vibrations of the personal alarm system exceeding preset times within a period of time.

7. The system of claim 6, wherein the alarm setting module further sends a timing stopping signal to the determining module when the condition to stop the alarm from sounding is the number of vibrations of the personal alarm system exceeding preset times within the period of time and the period of time being reached.

* * * * *